(12) United States Patent
White et al.

(10) Patent No.: US 8,799,023 B2
(45) Date of Patent: Aug. 5, 2014

(54) MASS CUSTOMIZATION FOR MANAGEMENT OF HEALTHCARE

(75) Inventors: William D White, San Diego, CA (US); Schumarry Chao, Santa Monica, CA (US)

(73) Assignee: MedImpact Healthcare Systems, Inc., San Diego, CA (US)

( * ) Notice: Subject to any disclaimer, the term of this patent is extended or adjusted under 35 U.S.C. 154(b) by 1611 days.

(21) Appl. No.: 10/372,052

(22) Filed: Feb. 21, 2003

(65) Prior Publication Data

US 2006/0178915 A1    Aug. 10, 2006

Related U.S. Application Data

(60) Provisional application No. 60/419,917, filed on Oct. 18, 2002, provisional application No. 60/424,643, filed on Nov. 7, 2002.

(51) Int. Cl.
*G06Q 40/00* (2012.01)
*G06Q 10/00* (2012.01)
*G06Q 50/00* (2012.01)

(52) U.S. Cl.
USPC ........................................ 705/4; 705/2; 705/3

(58) Field of Classification Search
USPC .......................................................... 705/2–4
See application file for complete search history.

(56) References Cited

U.S. PATENT DOCUMENTS

| | | | |
|---|---|---|---|
| 5,301,105 A * | 4/1994 | Cummings, Jr. .................. | 705/2 |
| 5,704,044 A | 12/1997 | Tarter et al. | |
| 5,737,539 A | 4/1998 | Edelson et al. | |
| 5,845,255 A | 12/1998 | Mayaud | |
| 6,108,635 A * | 8/2000 | Herren et al. ..................... | 705/2 |
| 6,195,612 B1 | 2/2001 | Pack-Harris | |
| 6,283,761 B1 * | 9/2001 | Joao .............................. | 434/236 |
| 7,165,077 B2 | 1/2007 | Kalies | |
| 7,490,047 B2 | 2/2009 | Brown et al. | |
| 7,505,917 B2 | 3/2009 | Howe et al. | |
| 2001/0037216 A1 | 11/2001 | Oscar et al. | |
| 2002/0049617 A1* | 4/2002 | Lencki et al. ..................... | 705/4 |
| 2002/0095316 A1* | 7/2002 | Toan et al. ........................ | 705/4 |
| 2002/0111832 A1 | 8/2002 | Judge | |
| 2002/0147617 A1 | 10/2002 | Schoenbaum et al. | |
| 2002/0169727 A1* | 11/2002 | Melnick et al. ............... | 705/400 |
| 2003/0154106 A1 | 8/2003 | Marks | |
| 2004/0073457 A1 | 4/2004 | Kalies | |
| 2004/0143171 A1 | 7/2004 | Kalies | |

(Continued)

FOREIGN PATENT DOCUMENTS

| WO | WO 95/24010 | 9/1995 |
|---|---|---|
| WO | WO 97/44752 | 11/1997 |

OTHER PUBLICATIONS

"Cost Sharing Stratagies for OHP Medical Services." pp. 1-5. Revised Jul. 5, 2001.*

(Continued)

*Primary Examiner* — Luke Gilligan
*Assistant Examiner* — Kristine Rapillo
(74) *Attorney, Agent, or Firm* — Davis Wright Tremaine LLP

(57) ABSTRACT

A healthcare mass customization infrastructure individualizes plan designs by incorporating demographics, income, drug history, medical history, lab values, and future genomic information for appropriate and affordable access to medications. The mass customization infrastructure results in quality outcomes for the patients, improved care and productivity for the providers, and lower medical costs for the payers.

1 Claim, 7 Drawing Sheets

(56) References Cited

U.S. PATENT DOCUMENTS

| | | |
|---|---|---|
| 2004/0143594 A1 | 7/2004 | Kalies |
| 2004/0148195 A1 | 7/2004 | Kalies |
| 2004/0148196 A1 | 7/2004 | Kalies |
| 2004/0148198 A1 | 7/2004 | Kalies |
| 2005/0065821 A1 | 3/2005 | Kalies, Jr. |
| 2005/0071193 A1 | 3/2005 | Kalies |
| 2006/0129357 A1 | 6/2006 | Francis et al. |
| 2006/0184391 A1 | 8/2006 | Barre et al. |
| 2006/0271402 A1 | 11/2006 | Rowe et al. |
| 2007/0050210 A1 | 3/2007 | Wiley, II |
| 2007/0106623 A1 | 5/2007 | Melnick et al. |
| 2007/0250341 A1 | 10/2007 | Howe et al. |
| 2008/0312956 A1 | 12/2008 | Momita et al. |
| 2009/0177490 A1 | 7/2009 | Howe et al. |
| 2010/0057489 A1 | 3/2010 | Howe et al. |
| 2010/0161351 A1 | 6/2010 | Howe et al. |
| 2010/0287002 A1 | 11/2010 | Barre et al. |
| 2011/0029321 A1 | 2/2011 | Rourke et al. |

OTHER PUBLICATIONS

"Cost-Sharing Strategies for OHP Medical Services", herein after Cost-Sharing (pp. 1-5. Revised Jul. 5, 2001.).*

PCT International Search Report, Jul. 8, 2007

Laing, et al, "Tuberculosis Drug Issues: Prices, Fixed Dose Combination Products and Second Line Drugs", Int. Journal Tuberculosis Disease, 2000, p. S194-S207, vol. 4, No. 12.

Huskamp, et al., "The Medicare Prescription Drug Benefit: How Will the Game Be Played?", Health Affairs, 2000, p. 8-23, vol. 19, No. 2.

Lipton, et al., "Managing the Pharmacy Benefit in Medicare HMOs: What Do We Really Know?", Health Affairs, 2000, p. 42-58, vol. 19, No. 2.

"Cost Sharing Strategies for OHP Medical Services." pp. 1-5. Revised Jul. 5, 2001.

Laing, R.O., et al., "Tuberculosis Drug Issues: Prices, Fixed Dose Combination Products and Second Line Drugs", Journal Tuberculosis Disease, 4(12) S194-S207 (Feb. 2000).

Huskamp, H.A., et al., "The Medicare Prescription Drug Benefit: How Will the Game be Played?" Health Affairs, 19(2) 8-23 (Mar.-Apr. 2000).

Lipton, H.L., et al., "Managing the Pharmacy Benefit in Medicare HMOs: What Do We Really Know?" Health Affairs, 19(2) 42-58 (Mar.-Apr. 2000).

MedImpact Medicare Part D 2009 Pre-Processing Drug List (PPDL) White Paper, Updated Mar. 25, 2008. pp. 1-5.

MedImpact Medicare Part D 2008 Pre-Processing Drug List (PPDL) White Paper, Updated Mar. 25, 2008. pp. 1-5.

MedImpact Medicare Part D Pre-Processing Drug List (PPDL) White Paper, Updated Jul. 20, 2006. pp. 1-5.

MedImpact Medicare Part D Drug List White Paper, Oct. 13, 2005. pp. 1-4.

* cited by examiner

MASS CUSTOMIZATION FOR MANAGEMENT OF HEALTHCARE

CROSS-REFERENCES TO RELATED APPLICATIONS

This application claims the benefit of priority under 35 U.S.C. 119(e) to provisional U.S. Patent Application No. 60/419,917, filed Oct. 18, 2002, and to provisional U.S. Patent Application No. 60/424,643, filed Nov. 7, 2002, which are incorporated herein by reference in their entirety.

FIELD OF THE INVENTION

This invention relates generally to management of healthcare systems, and more specifically to an infrastructure to individualize health plan design for appropriate and affordable access to medications for quality outcomes by incorporating demographics, income, drug history, medical history, lab values, and future genomic information into the plan design.

BACKGROUND OF THE INVENTION

Current healthcare plans present several problems for delivering effective health care to plan participants. The current healthcare plans are designed based upon a one-size-fits-all for every member of healthcare plans regardless of individual income, affordability, clinical history, or the appropriateness of care. These healthcare plans operate under ineffective resource allocation. Increasing costs are shared with consumers without considering the impact on other healthcare sectors, and financial incentives are misaligned amongst the stakeholders in health care.

There is a substantial disconnect between the most important relationship in health care, that is, the relationship between the patient/participant and the healthcare providers, i.e., physicians, pharmacists, and hospitals. The current healthcare system focuses on managing costs as opposed to improving healthcare outcomes, and optimizing individual segments of healthcare as opposed to optimizing the overall healthcare system. The current healthcare system also focuses on reactive as opposed to proactive healthcare delivery. Clinical trials of various therapies drive healthcare decisions as opposed to provider assessment of the quality of the outcomes. These inefficiencies and shortcomings of the current healthcare system leads to inefficient treatment of patients, including the aging population.

Until the 1980's, healthcare plan sponsors were able to manage the increases in annual healthcare premiums for their members. Managed care then appeared as a solution to continually rising healthcare costs in the United States. Managed care was an attempt at managing resources within healthcare, i.e., to allocate resources where needed. Although managed care was able to squeeze inefficiencies from healthcare delivery for a time, managed care had a fatal flaw in that substantially all of the focus was on managing costs rather than on managing healthcare outcomes, e.g., improving aggregate healthcare which would result in much more efficient utilization of healthcare resources.

Healthcare delivery remains fragmented resulting in suboptimal allocation of resources and substantial cost inefficiencies. For example, within prescription drug benefits, success is often measured by the ability to keep drug utilization down and to raise patient co-payments. However, this strategy is sub-optimal for a number of reasons. For example, those patients who cannot afford a large drug co-payment have a greater than average probability of ceasing to take their medications rather than filling their prescriptions. This oftentimes results in additional office visits to a physician, or, in some instances, hospitalization. Either circumstance results in a dramatic increase in aggregate healthcare costs. Thus, while pharmacy benefit programs are considered to be successful, the overall healthcare for patients is a failure.

Current healthcare systems have evolved around the medical model of reactive medicine. A patient has symptoms, visits a physician and is treated. To achieve optimal allocation of healthcare resources and dramatically improve healthcare outcomes, physicians must be empowered with detailed and current information about their covered patient populations so that the medical model can become proactive. The evolution of technology and medical research has provided the opportunity to identify patients with a high probability of contracting certain disease states in the future. This evolution has dramatic potential for improving healthcare outcomes and decreasing the increase in the annual cost of healthcare. However, the current healthcare system does not empower providers to offer the best of preventive medicine based upon the developing technology and medical research.

Several other unintended negative consequences have resulted from the managed care experience. A key failure of managed care is that the vital link for healthcare delivery between the physician and the patient has been broken. Although the primary care physicians are essential to delivering quality healthcare to patients, managed care has placed many roadblocks in front of the physicians by discouraging, and in some instances preventing, the delivery of quality healthcare services.

Another key failure of managed care is the misalignment of financial incentives. Resources have been taken away from healthcare providers in many instances and reallocated to non-providing healthcare entities whose primary purpose has been to aggregate healthcare supply and demand, that is, the provider networks and the patient populations. Providers' incentives to provide quality medical treatment have been curtailed significantly, resulting in many physicians' deciding to terminate the practice of medicine. A shortage of physicians is on the horizon due to the lack of incentives for providing quality healthcare.

Another failure of managed care is the inability to provide healthcare to an aging population. The aging population in the United States is beginning to utilize more healthcare resources at a time when many healthcare plan sponsors are curtailing or eliminating healthcare benefits for retired workers. Thus, increasing strains are placed on the already-over-taxed Medicare benefits system.

The current healthcare systems do not have an effective ability to deliver the bio-engineered pharmaceuticals of the future. The initial completion of mapping of the human genome is generating unprecedented research into drugs of the future to combat life-threatening disease. Many of these bio-engineered drugs are extremely expensive and require special administration by healthcare providers. Thus, healthcare systems must adapt to a model which matches utilization with need, that is, a balance between too much and not too little healthcare benefits.

Due to double digit increases in annual premiums and a soft labor market, a number of health plan sponsors give participants a fixed-dollar amount for health care during the year, and then allow the participants to choose a health plan in which to enroll. Although the fixed-dollar plan does give the participant greater choice, it does nothing to improve health care outcomes. Nor does the fixed-dollar plan empower the participant to know which plan is best for him or her. The plan choices typically represent a large number of different commercially available plans, and are not customized to the particular plan participant. Further, the providers are not empowered with tools to assist them in the delivery of higher quality health care. In addition, they are not kept in the loop as to what is happening to a given patient or an entire patient population assigned to them.

"Customized" health plans exist in the public domain which offer different participant premiums based upon limited aggregate income levels. However they are very limited in scope, and do not superimpose health history and current health over income to further refine plan design. Healthcare professionals are attempting to reduce the growth of healthcare expenditures by simply mandating cuts, or discouraging care through onerous and lengthy preauthorization or pre-certification processes. These controls do not solve the real problem of escalating healthcare costs.

Thus, a need remains for a healthcare infrastructure that delivers appropriate and affordable medication to participants. A further need remains for a healthcare infrastructure that applies current outcome research to healthcare plan design, and that provides up-to-the minute communication of healthcare episode data to providers to aid in their decision making. A need also remains to control healthcare expenditures by adopting and monitoring special programs focused on high-frequency healthcare episodes to reduce the volume of episodes to successfully treat a patient. Another need remains for a healthcare infrastructure that incorporates data platforms for capturing, managing, analyzing, simulating, and communicating information and action steps to be inclusive of all aspects of healthcare.

SUMMARY OF THE INVENTION

It is an advantage of the present invention to provide a healthcare infrastructure to individualize healthcare plan design for appropriate and affordable access to medications which results in quality healthcare outcomes by incorporating participant demographics, income, drug history, medical history, lab values, and future genomic information into the plan design.

It is another advantage to provide a healthcare infrastructure which includes process technology and information systems that constitute a back-end mechanism for automatically integrating, analyzing and mining participant-specific financial and clinical data to support participant decision-making at a point of sale of medications.

It is yet another advantage to provide a data infrastructure which serves as a back end of a mass customization infrastructure to provide information, and to align incentives among all key stakeholders in healthcare including the physicians, the pharmacists, the payers, the health plans and the plan participants/consumers.

Still another advantage is to provide a methodology to automatically influence behaviors of the plan participant based on individual income, clinical profile, evidence-based guidelines and protocols and, potentially, genetic profile, and to deter unnecessary utilization of medications while facilitating appropriate utilization of medications to optimize overall total cost and quality of health care.

It is still another advantage to provide an overall process which incorporates advanced financial and statistical risk management measures focused to reduce sponsor reinsurance premiums, and to enable statistically sound forecasts of future healthcare costs.

A further advantage is to provide a healthcare system that is based upon an outcome approach which extends to analyzing cost effectiveness, quality of life and individual patient outcomes.

The exemplary embodiment of the present invention provides a mass customization healthcare infrastructure which dramatically changes how healthcare is managed, delivered and improved. The mass customization of the exemplary embodiment focuses on the needs of the consumer by giving the consumer greater choice, while improving healthcare outcomes. The mass customization infrastructure empowers the consumer to know which plans are best for him or her, and customizes the plan choices for each plan participant. The mass customization infrastructure empowers the providers with tools that assist in the delivery of higher quality healthcare, and that maintain updated status of a given patient or an entire patient population.

The mass customization infrastructure of an exemplary embodiment includes a mass customization system accessible by providers, patients, payers, and partners. The providers include the physicians, pharmacists and hospitals. The patients are the healthcare participants that are enrolled in health plans sponsored by the payers, e.g., employers and insurance companies. The partners are the medical and pharmaceutical manufacturers and distributors. The mass customization system includes a healthcare data platform and analyzer which gathers information from a number of disparate sources. The data platform and analyzer performs data mining, statistical analysis, and Monte Carlo simulations for presenting the data in usable form. The gathered information and the results of the analyses are stored in a data warehouse of the system. The data warehouse is available to the providers, patient, payers and partners through a web interface platform which allows system users to view information. The data is also utilized by a number of programs managers, point of sale benefits managers, and prescription and claims managers. A smart card interface allows data exchange between the mass customization system and smart cards assigned to individual patients. The smart card may be used to verify healthcare history and prescriptions.

The mass customization infrastructure of the exemplary embodiment provides a vehicle for delivering comprehensive customization of health benefits at the individual level based upon each participant's income and unique health status. Customizing healthcare to the individual provides appropriate and affordable healthcare, meaning that the appropriate medications and care are supplied to the participant based upon the participant's healthcare information as well as the participant's ability to pay. The appropriate and affordable healthcare system of the exemplary embodiment gives each participant incentive to be involved in his or her healthcare by providing each participant with an individualized healthcare plan.

The healthcare plan for each participant is based upon the participant's profile including detailed health history, prior healthcare utilization, demographic data, income data, and current health treatments. The profile may be expanded to include future genomic information. The mass customization infrastructure utilizes this information to create a health plan for the participant based upon predicted utilization over a time period. The predicted utilization is compared to the actual utilization after the time period to determine whether to adjust plan rules, and/or to provide incentives to the participant, the providers, and the payers. The incentives are used to encourage positive healthcare behavior and treatments. A participant's co-payment amount is determined by a claims processing rules generator of the mass customization system based upon the participant's profile. The participant's share in the cost of his or her healthcare is determined in part by the participant's ability to pay.

The mass customization infrastructure manages the utilization of health plan benefits efficiently by providing access to the data warehouse for validating information and decreasing administrative costs because of regulations and potential liabilities. A patient is able to request medication and/or a provider is able to prescribe medications to address a current health concern. The patient presents the prescription to a pharmacy, and the mass customization system determines the appropriateness of the medication by automatically integrating, analyzing and mining participant-specific financial and clinical data. If the medication is appropriate for the current health concern, the patient may purchase the medication at a lower co-payment as determined by the claims processing rules generator of the system. If the medication is not appropriate, but not harmful to the patient, a high co-payment or a 100% co-payment is required for purchase of the medication. Thus, the medication prescribed by the physician is available to the patient immediately without the need to process pre-authorization forms.

Physicians of the existing healthcare system are rated solely by the level of resources they consume, and not by any measures which incorporate the "sickness" of the patient population they see. The mass customization infrastructure of the exemplary embodiment addresses this shortcoming of existing systems by aligning incentives among all key stakeholders in healthcare, including the physicians, the pharmacists, the payers, and the patients. Physicians are evaluated based upon the current health of the physicians' patient population, thereby making the physicians' overall quality assessment risk adjusted for the populations they see. In addition, physician behavior is positively influenced by taking away roadblocks from quality treatment, and by supporting the physicians in the manner in which they practice medicine.

The mass customization system of an exemplary embodiment aligns incentives to optimize physician performance and patient clinical outcomes. The physicians are supported in their decisions of prescribing appropriate medications and treatments to achieve good quality outcomes. Based upon the mass customization data claims processing, the patients' co-payment amounts are customized so that each patient can afford the necessary medications and treatments. The patients take the necessary medications and/or treatments, and thereby do not need emergency room and hospital services. In this way, the mass customization system averts the high costs for the health plan while ensuring a better quality of life for the patient. These outcomes are tracked by the mass customization system, and the physician's efforts of quality healthcare outcomes are rewarded.

The mass customization system of an exemplary embodiment of the present invention has a number of administrators and working units for managing the system, including a technology unit, a financial and statistical analysis unit, a communication unit, and a risk unit. The technology unit is responsible for integrating massive amounts of data from disparate sources throughout healthcare for use in mining, analysis, simulations, forecasting and decision making. The communications unit, which provides up-to-the-minute data and analysis for all healthcare stakeholders, is essential for communications between patients, providers, plan sponsors, and partners. The communication unit processes take maximum advantage of web portal technologies such as a patient provider sponsor web interface. The financial and statistical analysis unit is responsible for continual monitoring, assessing and interpreting the data as it is received, and translating the data into actionable information. The financial and statistical unit assesses outcomes, updates plan results, and generates health plan rules. The risk management unit manages risk sharing entities, such as captive insurance companies. Financial incentives and risk management processes work to reduce reinsurance premiums, and lower sponsor errors and omissions insurance premiums. With comprehensive up-to-the minute financial and statistical analysis of claims data, the risk management unit further impacts providers by consulting with them on their risk management operations.

BRIEF DESCRIPTION OF THE DRAWINGS

The present invention will be better understood from the following detailed description of a preferred embodiment of the invention, taken in conjunction with the accompanying drawings in which like reference numerals refer to like parts and in which.

DESCRIPTION OF THE PREFERRED EMBODIMENT

The following detailed description utilizes a number of acronyms, abbreviations, and terminologies which are generally well known in the art. While definitions are typically provided with the first instance of each term and acronym, for convenience, Table 1 below provides a list of the terminology/acronyms and their respective definitions.

TABLE 1

| TERMINOLOGY | |
|---|---|
| TERMINOLOGY/ ACRONYM | DEFINITION |
| CAD | Carotid Artery Disease |
| CHF | Congestive Heart Failure |
| COPD | Chronic Obstructive Pulmonary Disease |
| DSM | Disease State Management |
| DSTRBS | Distributors |
| DTC | Direct to Consumer |
| FDA | Food and Drug Administration |
| HMO | Health Maintenance Organization |
| Hx | History |
| LOS | Length of Stay |
| MFRS | Manufacturers |
| PA | Prior Authorization |
| PBM | Pharmacy Benefits Manager |

TABLE 1-continued

TERMINOLOGY

| TERMINOLOGY/ ACRONYM | DEFINITION |
| --- | --- |
| Partners | Medical and pharmaceutical manufacturers and distributors, and technology |
| Patients | Healthcare consumers |
| Providers | Physicians, pharmacists, hospitals |
| PPO | Preferred Provider Organizations |
| RC | Reasonable and Customary |
| Rx | Prescription |
| UCR | Usual, Customary, and Reasonable |

Figure 1:
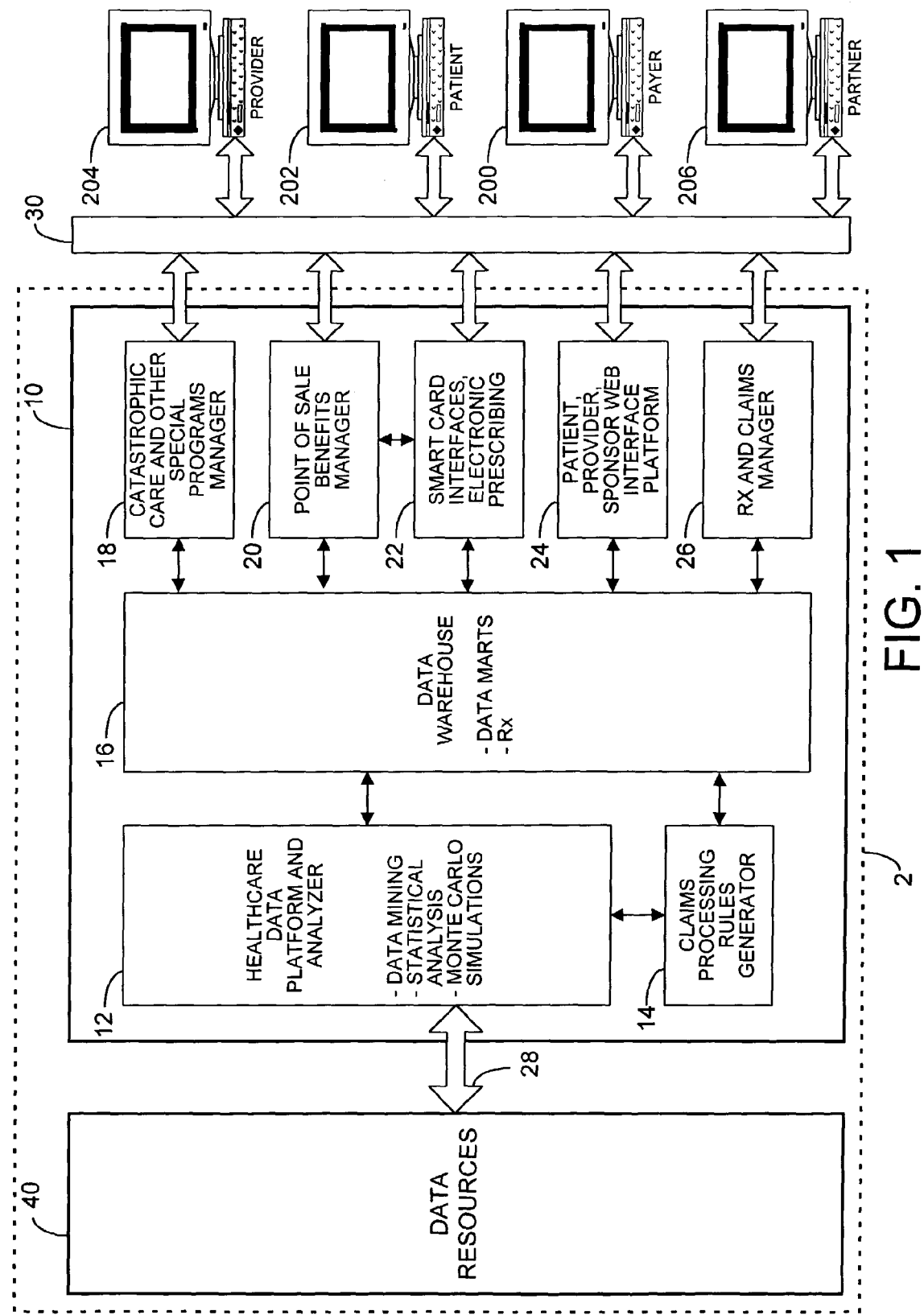
FIG. 1 is a block diagram of the mass customization infrastructure of a preferred embodiment.
Figure 7:
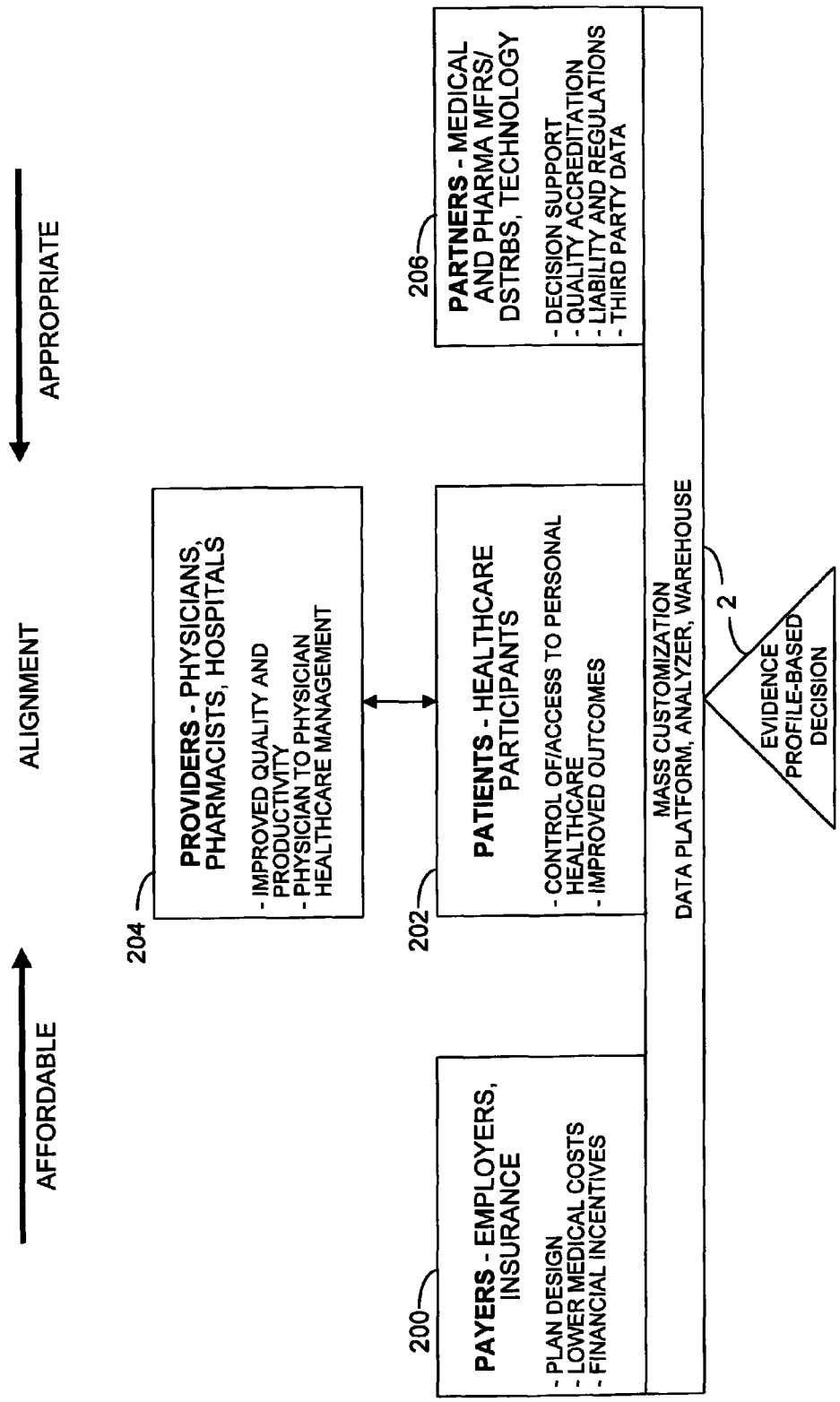
FIG. 7 illustrates an alignment between the needs of the providers, the patients, the payers and the partners of the healthcare system of a preferred embodiment of the present invention.

The mass customization infrastructure 2 of a preferred embodiment of the present invention, as illustrated in FIGS. 1 and 7, is a comprehensive system and process that substantially alters the way health plans are constructed and managed in the United States. Mass customization increases the wellness of patient populations 202 by re-aligning financial incentives within healthcare and by lifting the level of importance of the relationship between the patient 202 and primary care physician 204 to that of the most important touch point in healthcare.

Mass Customization Infrastructure.

FIG. 1 illustrates the mass customization infrastructure 2 for the management of healthcare of a preferred embodiment of the present invention. A healthcare data platform 12 of the preferred embodiment is a healthcare data delivery tool which accepts healthcare-specific data from a variety of data resources 40 which are made available to the healthcare data platform 12 through a data link 28 that may include an internet web link, a modem link, local area network, etc. The delivery tool 12 analyzes data and presents various usable forms of the data, e.g., high level data views summarizing trends. The analyzed data is stored in a data warehouse 16 for access and for use by user's 200, 202, 204, and 206 of the mass customization infrastructure 2.

As illustrated in FIG. 7, the user's of the mass customization infrastructure 2 of the preferred embodiment include the patients 202, the providers 204, the payers 200, and the partners 206. The mass customization infrastructure 2 balances, i.e., optimizes, the expectations of the payers 200 and the partners 206 to place the focus of healthcare on the patients 202, and on the relationship between the patients 202 and the providers 204. The patients 202 are the healthcare participants who have received healthcare benefits through, for example, their employers, or participating in health maintenance organizations (HMO), preferred provider organizations (PPO), etc. The providers 204 are typically the physicians, pharmacists, and hospitals that provide "care" to the patients. The partners 206 are the medical and pharmaceutical manufacturers, vendors and distributors, and other healthcare technology providers. The payers 200 are the employers, the insurance companies, the case managers, brokers and other entities which pay the costs of the healthcare provided to the patients 202.

Typically, in the present healthcare systems, the partners 206 want the patients 202 to be provided with the newest non-generic medications, technologies, and pre-emptive healthcare, while the payers want the patients 202 to receive the least expensive solutions to existing healthcare issues. The providers 204 are limited in what they may provide to the patients 202 due to the constraints imposed on them by the payers 200 of managed care. The mass customization infrastructure 2 utilizes evidence and profile based decisions to align the objectives of the payers 200, the providers 204, and the partners 206 such that the patients 202 receive the most appropriate and affordable healthcare as explained further below.

Figure 4:
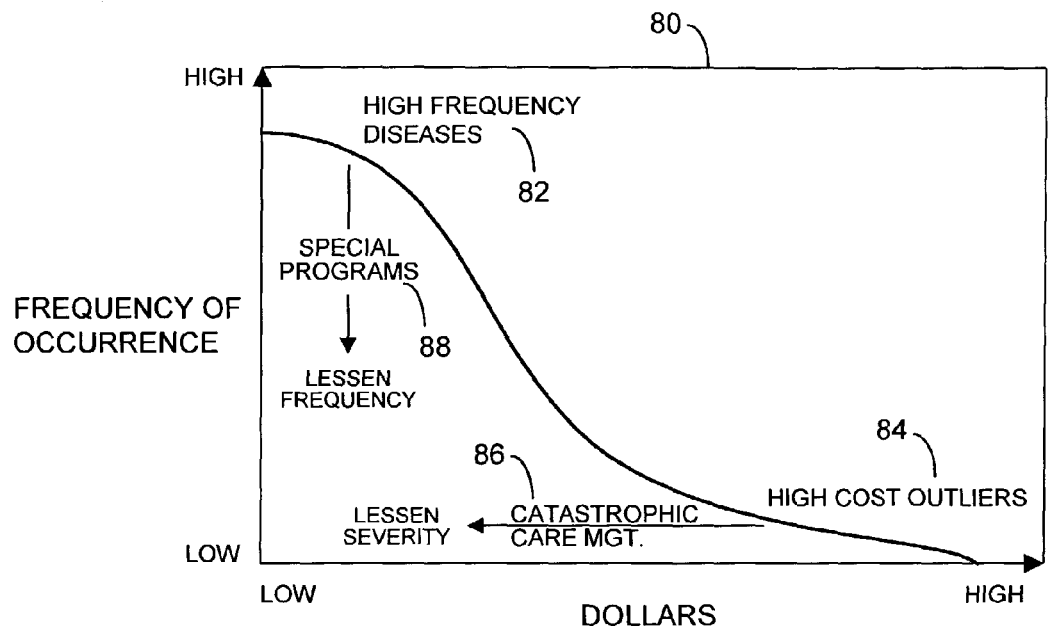
FIG. 4 is an illustration of a statistical distribution of outcomes.

FIG. 4 illustrates the objectives 80 of the mass customization infrastructure 2 of lowering the frequency of healthcare encounters and lowering healthcare dollar output by constraining the level and frequency of outlier healthcare events. High frequency diseases 82 include asthma, diabetes, high blood pressure, mood disorders, etc. Although the cost is low to provide medications to the patient, the current healthcare system does little or nothing to prevent the high frequency diseases 82. The mass customization infrastructure 2 of the present invention decreases the occurrences of the high frequency diseases by focusing on outcomes of patient healthcare. The use of special programs 88 are utilized to provide preventive healthcare to patients. Continuing with FIG. 4, in addition to lowering frequency of occurrences of disease, the present invention lowers high cost expenditures. A patient whose length of stay in a medical facility or whose treatment cost differs substantially from the stays or costs of most other patients in a diagnosis related group is referred to as an "outlier" patient. High cost outliers 84 include neonates and patients having cancer, heart problems, burns, etc. The mass customization infrastructure 2 lessens the severity of high cost outlier episodes through use of catastrophic care management 86.

Referring again to FIG. 1, the healthcare data platform and analyzer 12 integrates data from all segments of healthcare utilizing advanced data mining, high level statistical analysis, Monte Carlo simulations and decision making, and delivers actionable information accessible through the data warehouse 16 of the infrastructure 2. An example of a healthcare data platform 12 that may be used with the present invention is "Medinitiatives Inform" that is available through MedInitiatives, Inc. The robust data platform 12 of a preferred embodiment of the invention monitors all received healthcare data 40 and scientifically alerts the healthcare users 200, 204, 206, 208 to new or changing relationships that call for immediate patient intervention or possibly an amendment in overall healthcare benefits offered by a plan sponsor 200. The mass customization infrastructure 2 processes all "discovered" relationships through high-level statistical analysis to ensure that potential actionable data is statistically significant. The application of advanced Monte Carlo simulation and forecasting techniques enables the system 2 to simulate future healthcare utilization and patient outcomes, and assists the plan sponsor in effectively managing the healthcare plan in the future.

Figure 2:
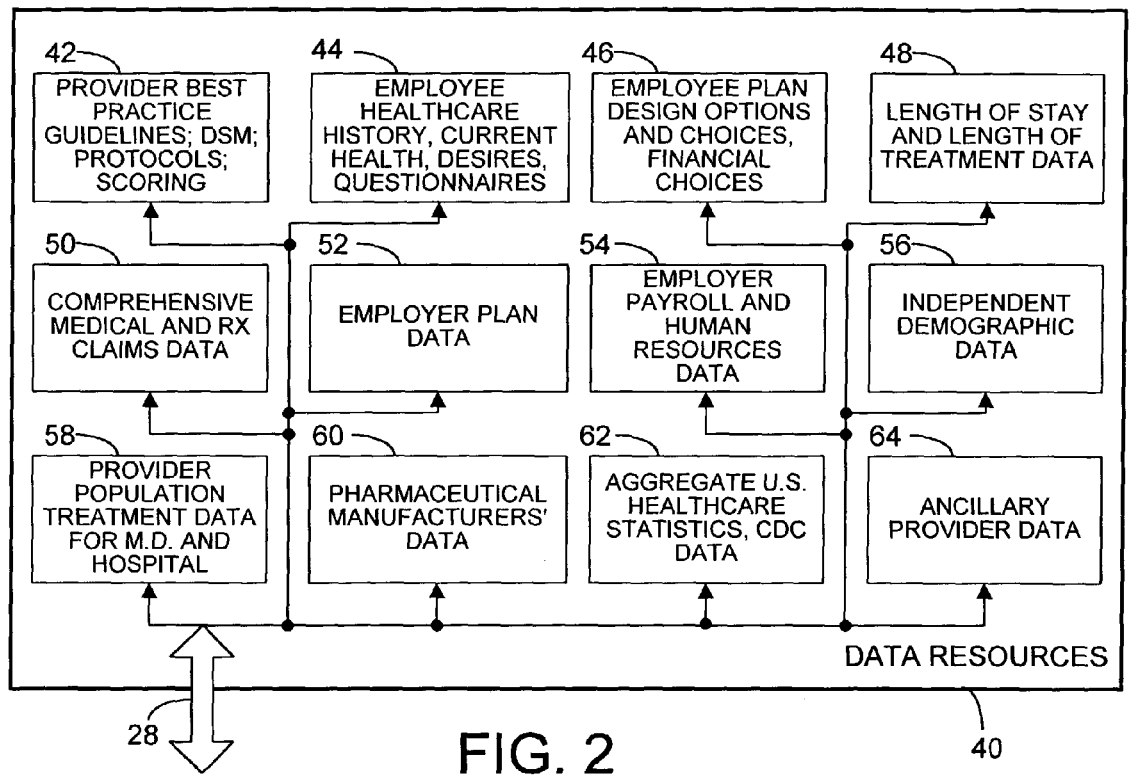
FIG. 2 is a block diagram of the data sources for use with a preferred embodiment of the mass customization infrastructure of the present invention.

FIG. 2 illustrates various data resources that may be utilized by the mass customization infrastructure of the preferred embodiment. Data received from the partners 206 includes data from pharmaceutical manufacturers 60 which provides information on medication usage, indications, etc. This data may include real world outcomes data, as opposed to clinical trials, and market share information from various potential drug formulary, compliance, and generic thug-switching strategies. Other third party data includes independent demographic data 56, e.g., statistics on disease occurrence within a particular demographic segment, and aggregate U.S. healthcare statistics and CDC data 62. Data received from the providers 204 includes best practice guidelines, disease sate management (DSM), protocols and scoring 42, length of stay and length of treatment data 48, comprehensive medical and prescription claims data 50, population treatment data for medical doctors and hospitals 58, and any ancillary provider data 64. Data received from the payers 200 includes employee healthcare history, current health, desires, and questionnaires 44, employee plan design options and choices, and financial choices 46, employers plan data 52, and employer payroll and human resources data 54.

The data warehouse 16 is accessible to various managers 18, 20 and interfaces 22, 24, 26 for use by business analysts 206, medical directors 204, pharmacy directors 204, and case managers 200 for information to improve business performance and quality of care. The infrastructure provides healthcare professionals 204 with access to participant-defined data views and instantaneous ad hoc queries in real-time calls to the data warehouse 16. These data views provide summaries and detailed information on, for example, key performance indicators, diseases, drugs, pharmacies, prescribers, members, and utilization. The infrastructure 2 provides the data and information 16 which enables an individual participant 202 to customize his or her health plan around income and unique health situations through direct access to the infrastructure or through an employer or other payer 200. The mass customization infrastructure 2 utilizes state-of-the-art web portal technology to send/receive information to/from the participants 202, the providers 204, the payers 200 and the vendors 206.

A patient, provider, sponsor web interface platform 24 is designed for patient, provider and plan sponsor communications via a network 30, e.g., the Internet. The platform 24 provides an interface with the payers 200, such as the plan sponsor's human resources and payroll departments, to obtain the income and demographics data that is essential in customizing healthcare. The platform 24 is designed to allow the participant 202 to view all aspects of his or her healthcare on one platform, including physician visits, prescription drug utilization, hospitalization, catastrophic healthcare management, special programs for high-frequency healthcare episodes, etc. The participant is also provided access to announcements, health program calendars, provider directories and educational materials from a single source. The access to healthcare information and options not only empowers participants, but also assists providers in strengthening participants' therapies.

The sponsor web interface platform 24 enables providers 204 and payers 200 to perform transactions, to download information, to make changes to demographic and account information, and to monitor and analyze each sub-sector of healthcare as well as overall healthcare of patients 202. This platform provides the tools necessary for identification of actionable processes within healthcare to further optimize utilization and manage resources. The interface platform 24 also decreases service costs by allowing participants 202 to use their computer for many inquiries and transactions that previously required phone calls to service centers of the applicable healthcare organization. An example of a sponsor web interface platform that may be used with the present invention is "@bovehealth" provided by Verilet, Inc.

The point of sale benefits manager 20 represents the interface between the participant 202, a point of sale such as a pharmacy, and the mass customization infrastructure 2. The point of sale benefits manager 20 expands prescription processing to incorporate all facets of healthcare through the link to the data warehouse 16 of the infrastructure 2. A prescription drug program available to the point of sale benefits manager 20 monitors on-label versus off-label usage of prescription drugs to ensure optimal healthcare is delivered. The integrated technology platform of the mass customization system 2 is capable of alerting participants 202, pharmacists 204 and physicians 204 of potential negative drug interactions, drug recalls, allergy sensitivities or other healthcare concerns. Through auto queries into the participant's medical and lab data, determinations are made if a prescription drug has a potential to be harmful. For example, if a participant 202 is purchasing medications from a pharmacy 204, the benefits manager 20 alerts the pharmacist as to other medications that the participant 202 is taking that may render the purchased medication ineffective.

Existing platforms that have been used exclusively for prescription drug benefits processing and prescription drug plan administration may be utilized with the mass customization infrastructure 2 by incorporating specialized health improvement plans, such as direct to consumer (DTC) communications programs, to assist in the optimization of delivery of drug benefits and to better align drug benefit utilization with needs. The link between the providers 204, such as the pharmacists, and the infrastructure data warehouse 16 results in improved healthcare outcomes.

Figure 5:
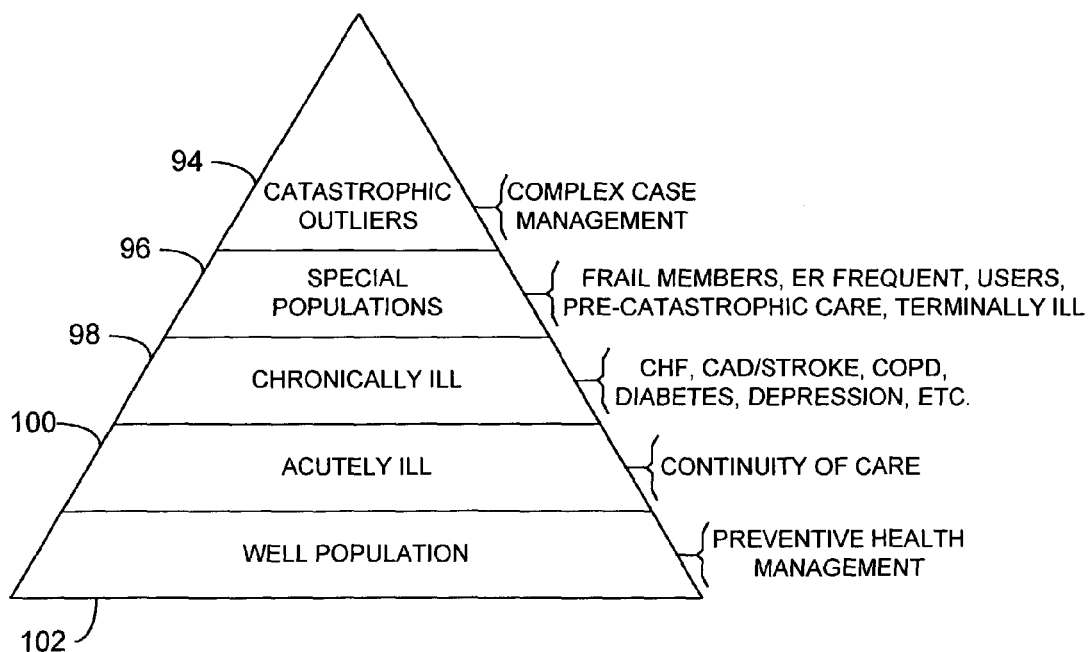
FIG. 5 shows a healthcare pyramid for healthcare case management of a preferred embodiment.

The mass customization infrastructure 2 includes catastrophic care and special programs managers 18 for integrating specific segments of healthcare with the infrastructure 2. FIG. 5 illustrates segments of the healthcare population that may require special programs provided by the infrastructure 2. The healthcare population consists mainly of "well" participants 102. The mass customization infrastructure 2 supports the well population 102 by providing preventive healthcare management programs. Preventive healthcare management may include, for example, ongoing education about healthy lifestyles, etc. Other patients who have been identified as possessing certain disease state "markers", and who do not currently have a targeted disease state, but have been identified as having a high probability of incurring such disease state, are monitored. At certain predetermined levels, the primary care physician 204 is alerted and educational information is provided to the patient by, for example, electronic mail. A hard copy is available for those who do not have Internet access.

A manager for acutely ill patients 100 provides on-going management for treatment of patients that are identified as having special healthcare requirements. The provider's 204 access to the results of the data mining and analysis 12 enables the provider 204, in conjunction with the system 2, to "red flag" those patients with high frequency and/or acute episodes. These patients 202 may include catastrophic outliers and patients who are generating high or recurring healthcare costs, whatever the reason. For example, the system 2 alerts the physician 204 to the healthcare status of older frail patients 202 who may have multiple office visits within a certain time period. The continuous collection and updating of data assists the physician 204 in identifying appropriate further action that should be taken for these flagged patients 202.

Continuing with FIG. 5, there are a number of "chronically ill" disease states 98 which consume substantial healthcare resources over time due to the volume of healthcare episodes required for treatment. While each healthcare episode may not be excessive in cost, continued healthcare utilization amounts to substantial resource utilization. The chronically ill population 98 includes those patients having, for example, diabetes, depression, hypertension, high cholesterol, multiple sclerosis, hepatitis C, respiratory diseases, congestive heart failure (CHF), certain digestive diseases, carotid artery disease (CAD)/stroke, and chronic obstructive pulmonary disease (COPD). These patients require programs that ensure the proper medications and care are administered on an ongoing basis to prevent deterioration into a higher level of care category. Patients within these chronic disease state categories are put under management of board approved protocols, and their progress is monitored distinct from the overall well patient population 102. Any important events are immediately communicated to the providing physician 204.

The healthcare population also includes "special" populations 96 that require provider-intensive ongoing care. The special population 96 includes emergency room frequenters, drug users, pre-catastrophic care patients, and the terminally ill. Other patients, currently under treatment, who are consuming substantial healthcare resources, are also put under special monitoring. The physician 204 is alerted based upon certain markers, and again, the special population patients 96 are provided education to assist them in managing their healthcare situations. The mass customization infrastructure also may be utilized to substantially assist providers 204 with patients having multiple disease states by quantitatively assessing treatment methodologies and by providing complete data to assist the provider in achieving positive healthcare outcomes.

Complex case management 94 applies to high cost catastrophic outliers. The top five claims areas for domestic reinsurance companies in the United States involve catastrophic care of neonates, cardiac events, cancer, organ transplants and burns/trauma. These healthcare outlier events 94 consume large amounts of healthcare resources and, as a result, raise significantly healthcare reinsurance premiums for plan sponsors who must limit their plan financial exposure. The mass customization system 2, identifies capable specialty provider management in each of these areas, and mandates their usage within a certain geographic population. Catastrophic expenses can be reduced 20% or more by utilizing and closely monitoring these specialty providers. Additionally, sponsor reinsurance premiums can be reduced through adoption of these programs and coordination with the reinsurance carrier.

Identification of the various patient populations 94, 96, 98, 100, 102, as illustrated in FIG. 5, are made through the use of the healthcare data platform 12, as described above. The data platform 12 integrates medical data and provides total ad hoc functionality so users 202, 204 can look at clinical data in a variety of multi-dimensional views with access to all the data in the data warehouse 16. The platform 12 is a data analysis tool that enables payers 200 and providers 204 to identify high-risk members. The platform 12 further provides details of aberrant therapy trends on a physician-specific and member-specific level. High-risk members in need of specific screening or more intensive case management, whether disease-based or due to inappropriate, correctable therapy, are quickly identifiable through the use of the system 2. The healthcare data platform 12 compares screens claims data against best care/clinical guidelines and pinpoints instances of guideline failures with real-time access to the data warehouse 16. Beyond reporting, this tool 12 allows applicable data to be accessed by patients 202, physicians 204, and pharmacies 204. In addition, any granular element of data may be scrutinized to initiate change for improved outcomes of patients 202.

Referring again to FIG. 1, although the use of smart cards exists in healthcare systems, the manner in which they are used is not optimal. The mass customization infrastructure 2 of the present invention provides smart card interfaces 22 as a front end application to facilitate data transfer between the card and the mass customization data warehouse 16, and to facilitate payment for health care services through the prescription and claims manager 26. The patient's entire healthcare history, utilization and enrollment data, current medications, etc., may be stored on the card and updated with each use of the card. Updating includes both the transfer of data from the card to the database 16 and from the database 16 to the card. The card may be presented to a physician for updating the physician's records, and may be presented to a pharmacist for verification of drug benefits. In addition, the card may be used as a healthcare debit card that is "refreshed" by plan sponsor contributions. Pharmaceutical transactions are simplified and speeded as the pharmacist receives authorization by swiping the patient's card. A patient's physician office visits and hospitalizations may be paid for via card swipe, as well.

Continuing with FIG. 1, the mass customization infrastructure includes a claims processor rules generator 14 in communication with the healthcare data platform and analyzer 12 and the data warehouse 16. The generator 14 automatically generates claims rules for each participant 202 based upon the ongoing analysis of the analyzer 12 and the data available in the data warehouse 16 and from the data resources 40. The claims processing rules generator 14 provides the amount of payment required from the payer 200 and the amount of co-payment from the participant 202. The payment/co-payment amounts may change every time information and data are updated and/or input into the system 2. The generated rules are available to, for example, the point of sale benefits manager 20 and the prescription and claims manager 26, through the data warehouse 16.

The prescription and claims manager 26 of the preferred embodiment manages pharmacy and third party claims. Unlike existing claims processing, the prescription and claims manager 26 of the present invention accesses the most current claims processing rules generated by the claims processing rules generator 14 and stored in the data warehouse 16. The prescription and claims manager 16 of a preferred embodiment may perform a number of functions including setup and maintenance of pharmacy claims data, setup and maintenance of physician claims data, review of benefit structures of each patient/participant 202 for proper claim adjudication, and periodic, e.g., biweekly, payments from the payer 200 to the provider 204.

Plan Customization for Appropriate and Affordable Healthcare.

Referring to FIGS. 1 and 2, in a preferred embodiment of the present invention, comprehensive customization of health benefits at the individual level is based on each participant's income and unique health status in order to customize healthcare around the individual plan participant 202. Customizing healthcare to the individual provides appropriate and affordable healthcare for each participant 202. "Appropriate" refers to providing the participant 202 with the appropriate medications and care based upon the participant's up-to-the-minute healthcare episode information, history, diagnostics, etc. "Affordable" refers to ensuring that the appropriate medications and care are accessible to the participant 202 based upon the participants' unique financial and clinical status. Through the use of appropriate and affordable healthcare, a participant 202 is given incentive to be involved proactively in his or her own healthcare.

Figure 9:
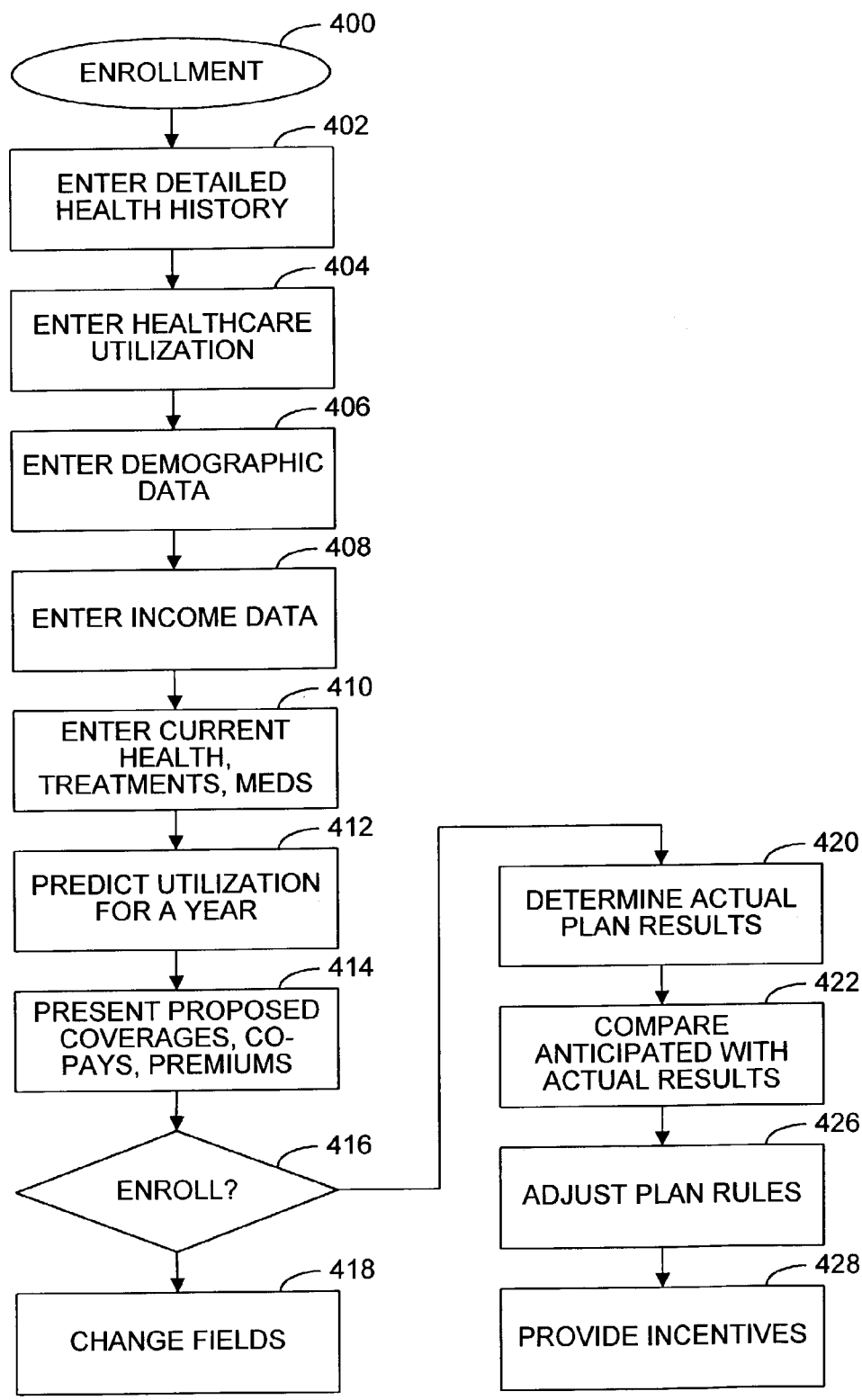
FIG. 9 shows a process for plan enrollment and adjustment.

The mass customization infrastructure 2 of a preferred embodiment allows many different standard plan options to be offered to the individual participant 202. When a plan participant 202 enrolls in a mass customization plan option through his or her employer 200, several different groups of queries are made, as illustrated in FIG. 9. A first step in an enrollment process 400 of one embodiment of the invention is to obtain a detailed health history 402 of the participant, and to enter the participant 202 into the data warehouse database 16. The database 16 is always available to the participant 202 via secure Internet 30 access. The database 16 also is available to the participant's primary care physician and specialists 204, when necessary, either on the Internet 30 or in printed form. In addition to the detailed health history, the complete healthcare utilization 404 and demographic data 406 of the patient 202 is entered into the database 16, having been extracted from disparate claims processing systems, e.g., through the prescription and claims manager 26 income data is entered at step 408.

As mentioned above, the participant 202, via secure Internet access 30 can view his or her entire utilization of all healthcare resources. The treating physicians 204 can instantly view this data, and/or have it printed out in their offices in complete or in daily chart form, customized to their individual practice styles. This access to data empowers the provider 204 with up to date complete information on the patient 202. This information includes laboratory data as well as diagnostic imaging stored on optical storage devices. The patient's 202 vital signs history is included, as well. To find out more about a disease state for which the participant 202 is currently being treated, he or she can obtain detailed information as well as answers on many general health topics via the Internet portal 30. General health information is provided through the data warehouse 16 which receives information from data resources 40, or through links to other content providers.

Referring again to FIG. 9, once health history, utilization, demographic and income data have been loaded onto the database, the participant 202 is queried about current health, physician treatments underway and prescription drugs currently being taken 410. The system healthcare data platform and analyzer 12 then reviews all data on the system surrounding the participant 202. Healthcare utilization is predicted 412 for the next twelve months using actual data as well as simulations from certain potential disease "markers" in the data. At step 414, the participant 202 then views the proposed coverages, co-payments, premiums, deductibles, maximum annual out-of-pocket charges for each individual and for the entire family. This screen is fully customized for the individual participant 202 and any dependents, and includes the maximum lifetime benefits. The participant 202 can then elect to enroll 416 and the system 2 automatically updates all fields for the choices. The participant 202 may elect to change 418 any of the financial fields, excluding lifetime benefit maximums and coverages. For example, a participant who does not want larger co-payments and deductibles may elect slightly higher monthly premiums to lower these two items.

After a predetermined time period, e.g., a one year's experience with each plan implementation, actual plan results are determined 420. Financial results are weighed against the anticipated results 422. Should the plan be on target, a portion of the allocated financial pool will be allocated by a statistical mechanism to participants 202 as a financial incentive for staying active in his or her healthcare 428, i.e., usage of an communication with the system 2. In one embodiment of the invention, a financial mechanism, such as a credit against the subsequent year's healthcare premium, is offered to the participant 202 for maximum positive marketing impact. Actual plan results that are "negative" also trigger whether the plan requires adjustment 426. Adjustments may include updating the plan rules, providing the participant with educational material, or assigning the participant to special programs, etc.

Cost Share Determination.

As discussed above, the participant's 202 personal demographic data and income from the human resources and payroll departments 54 is added in a private and secure fashion to the database of the data warehouse 16, as shown in FIGS. 1 and 2. This demographic data is essential, as the cost of benefits to the participant 202 varies depending upon the individual participant's income. Research illustrates that approximately 85% of aggregate healthcare expenditures are consumed by the sickest 10% of covered patients. A disproportionate amount of these sick patients are at the lower income levels. Evidence shows that lower income participants, on balance, do not have equal access to overall healthcare resources, healthcare education and preventive therapies.

An employer sponsored health plan 200 of the present invention spreads the risk of healthcare costs amongst the population of participants 202 to obtain overall healthcare utilization that is ideally similar to aggregate overall United States healthcare performance. Providing quality healthcare to the lower income segments of a plan population, oftentimes by lowering co-payments, deductibles, maximum annual out-of-pocket expenditures, etc., encourages treatment by those otherwise incapable or unwilling to continue therapies. This focus has dramatic positive impact on overall healthcare by eliminating potential additional physician visits and hospitalizations. In addition medical costs are lowered while improving quality of care, patient outcomes, and provider productivity.

Figure 3:
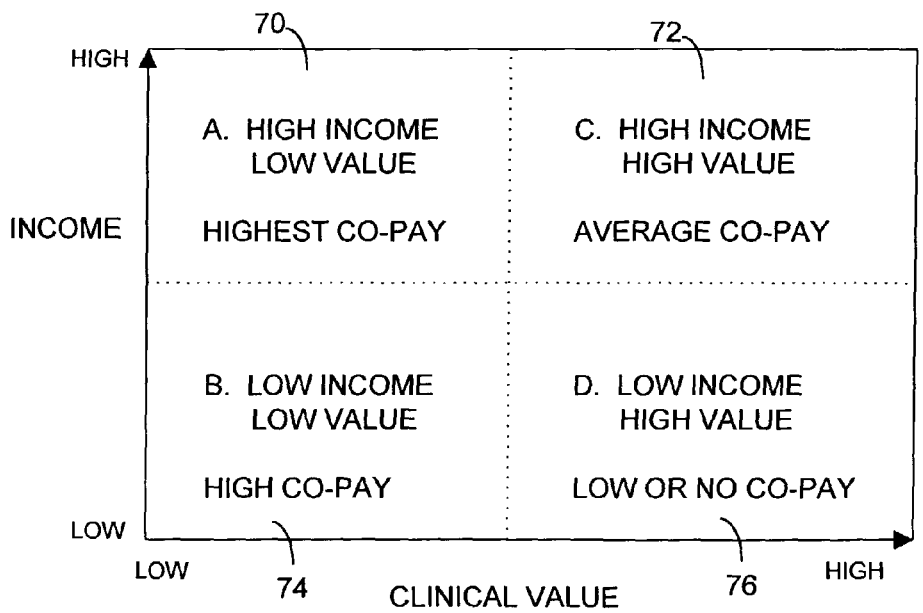
FIG. 3 illustrates cost share determination for income versus clinical value.

FIG. 3 illustrates a cost share determination of the mass customization infrastructure of the preferred embodiment. A participant's co-payment amount is determined by the claims processing rules generator 14 and is based upon the participant's profile, including pharmacy history, risk assessment, and genomics, the clinical indications, including clinical trials, medical outcomes, and Federal Drug Administration (FDA) label indications, and employer profiles, including financials, and demographics. As shown in FIG. 3, a low income participant 202 requesting a medication, therapy, or treatment of high value 76 has a low co-payment or a no co-payment. A low income participant 202 requesting a medication, therapy, or treatment of low value 74 has a high co-payment. A high income participant 202 requesting a medication, therapy, or treatment of high value 72 is required to pay an average co-payment. A high income participant 202 requesting a medication, therapy, or treatment of low value 70 is required to pay a highest co-payment amount. The income versus clinical value determination encourages the use of high value medications, therapies, or treatments by offering the low income and the high income participants 202 low co-payment amounts that are in line with the participant's ability to pay. In contrast, medications that are requested by the participant 202 that have low value are discouraged by requiring a higher co-payment. The following examples, with reference to FIG. 3, illustrate the benefits of the mass customization infrastructure 2 to deliver appropriate and affordable healthcare to participants 202.

In a low income, high value example, the mass customization analysis 12 determines that a patient Susan D. falls into the low income, high value profile 76 of the cost share determination shown in FIG. 3. The mass customization data base contains the demographic profile for Susan D. as shown in Table 2. A medical and drug history for Susan D. supports the use of the prescribed or requested treatment, resulting in a high clinical value. The treatment drug has prior authorization for Susan's health plan, and is approved for the current situation. Susan can afford to pay a low co-payment, e.g., $10, and purchases the drug. A possible result is that the employer avoids paying costs for hospitalization, and Susan D. avoids missing work.

TABLE 2

LOW OR NO Co-payment
SUSAN D.

| | |
|---|---|
| Sex: Female | Annual Income: $35,000 |
| Race: Caucasian | Medical History: Ulcer, GI bleed |
| Age: 36 | Requested Treatment: Celebrex ® |
| Marital Status: Single | Co-payment: Low or no co-payment |
| Dependents: 4 | |

In a high income, low value example, the mass customization analysis determines that a patient Larry M. falls into the high income, low value profile 70 of the cost share determination shown in FIG. 3. The mass customization data base contains the demographic profile for Larry M. as shown in Table 3. A medical and drug history does not support the use of the prescribed or requested treatment, resulting in a low clinical value. Thus, if Larry M. wishes to use the drug, he is allowed access to the drug, but must pay a 100% co-payment. In this example, the employer avoids paying for a drug that is not needed.

TABLE 3

HIGHEST Co-payment
Larry M.

| | |
|---|---|
| Sex: Male | Annual Income: $125,000 |
| Race: Caucasian | Medical History: No GI or bleeding |
| Age: 35 | Requested Treatment: Celebrex ® |
| Marital Status: Married | Co-payment: Highest co-payment |
| Dependents: 2 | |

Utilization Management.

The management of the utilization of benefits is inefficient and labor intensive because of the inability to validate information, the cost of provider and employee relations management, and the increasing administrative costs due to regulations and potential liabilities. For example, in a scenario of an existing healthcare system, a patient visits his physician to request an expensive drug after seeing a drug commercial. The physician prescribes the drug at the patient's request. The patient goes to a pharmacy and presents his eligibility card and the physician's prescription. The pharmacy submits eligibility and prescription information to a pharmacy benefits manager (PBM), which notifies the pharmacy that the drug requires a prior authorization. The patient then either has a choice to pay full price for the drug or to ask the physician to fill out a prior authorization form. The patient opts to call the physician, and asks that the physician submit a prior authorization request so that patient can pay a lower co-payment for the drug. The PBM sends a prior authorization form to the physician, who fills out the prior authorization, often inaccurately, to complete the prior authorization process. The information on the prior authorization form usually cannot be verified due to lack of data. The patient is notified by the PBM that the prior authorization has been approved. The patient returns to the pharmacy to buy the drug at the lower co-payment. Although the patient ultimately receives the drug, the prior authorization process is laborious, time consuming for both the physician and the patient, and costly, often at $25-50 per prior authorization.

Figure 6:
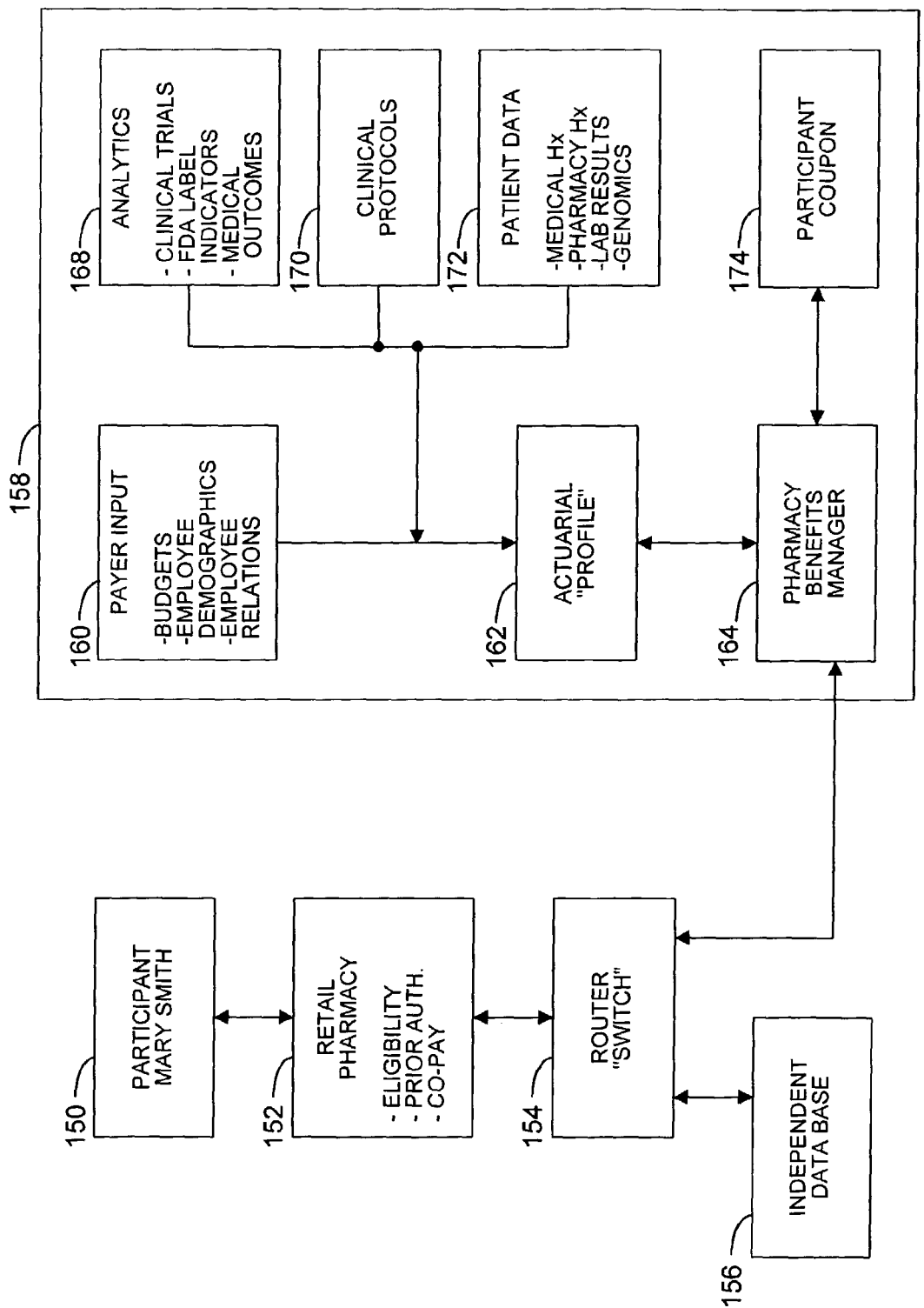
FIG. 6 illustrates a front end adjudication process and a back end incentive process of a preferred embodiment.

In the mass customization system 158 of an embodiment of the present invention, as shown in FIG. 6, co-payments are automated to drive appropriate utilization for individual patients. Mary Smith 150, after seeing a drug commercial, visits her physician to request the expensive drug in the commercial. The physician prescribes the drug at Mary's request. Mary proceeds to the pharmacy 152 and presents her eligibility card and the prescription. The pharmacy 152 submits the eligibility and prescription information to the pharmacy benefits manager 164 of a mass customization system 158 via a network connection 154. An independent data base 156 forwards any information concerning the drug to the pharmacy 152. The pharmacy benefits manager 164, based on the data analysis, i.e., the actuarial profile 162 for Mary Smith 150, derived from payer input 160, analytics 168, clinical protocols 170, and patient data 172, informs the pharmacy 152 of the appropriate co-payment for Mary 150.

Depending on the individual patient's actuarial profile 162, the co-payment may range from zero to 100%. If the drug is one that is appropriate for Mary's current health concern, her co-payment will be such that the co-payment does not deter purchase and utilization of the drug, and she pays the co-payment and takes the drug. If the drug is one that is inappropriate for her current health concern, Mary's co-payment is sufficiently high to encourage her to re-think whether she really wants to pay that much for the drug. If she wants the drug and can afford it, she may pay for it anyway. If she doesn't want to pay for it, she will not suffer adverse consequences since she doesn't need the drug. In either case, the health plan or payer 200, as shown in FIG. 1, is not liable for the cost. Utilization of the mass customization infrastructure 158 eliminates the costly prior authorization process and reduces hassles for the physicians and patients, while deterring unnecessary utilization. In addition the co-payment determined by the mass customization infrastructure 158 acts as an incentive or a disincentive for appropriate access to medication.

Continuing with FIG. 6, in one embodiment of the invention, the mass customization system 158 makes coupons 174 available to the participant 150. The pharmacy benefits manager 164 generates the coupon after receiving the actuarial profile 162 for the participant 158. The coupons 174 may be sent to the participant electronically or via mail. The coupons 174 may be for general medication purchase, or may be specific to a targeted medication based upon the profile 162. The coupons 174 may also be accompanied by education material. The participant 150 presents the coupons 174 to the pharmacy 152 to purchase medications. The use of coupons 174 creates an additional incentive for the participant 150 to purchase needed medications, and the outcome, i.e., the health of the participant, remains the focus of the mass customization system 158.

Healthcare Provider Incentive and Empowerment.

Referring again to FIGS. 1 and 7, the communications processes of the mass customization system 2 empowers the physician to provide top quality therapies to covered patients 202. Instant access of complete medical histories, entire claims histories, prescription drug utilization, specialist visits, laboratory reports, vital signs tracking, optically-stored diagnostic images, and summary reports are available from the mass customization data warehouse 16 simply by clicking on the patient's name through a web interface platform 24. Availability of information improves the physician's opportunity to deliver quality treatments.

The mass customization infrastructure 2 empowers physicians 204 to provide top quality therapies to covered patients 202 utilizing the continuously updated patient information that is inclusive of all areas of healthcare. The physician 204 is able to manage catastrophic outlier health care risks, high frequency disease states, multiple disease states, patients consuming above average healthcare resources, and behavioral health programs utilizing special programs with evidence-based guidelines and protocols to improve outcomes. As shown in FIG. 7, the mass customization system 2 balances healthcare to maintain the focus of healthcare on the relationship between the providers 204 and the patients 202.

Attempts by existing healthcare systems to change provider behavior have failed. For example, threats of transferring patients, lowering payments, etc., have proven ineffective tools to change the behavior of the treating physician. The mass customization infrastructure 2 makes it is possible to positively influence physician behavior by taking away roadblocks from quality treatment, and by supplying the physician 204 in the manner in which he or she practices medicine. Financial incentives reward the physicians 204 for quality healthcare outcomes.

A justifiable complaint by physicians of the existing healthcare system is that the physicians are rated solely by the level of resources they consume, and not by any measures which incorporate the "sickness" of the patient population they see. The mass customization infrastructure 2 addresses this complaint by evaluating a physician 204 based on a score which weights a physician 204 visit by a "sickness" coefficient, thereby adjusting a physician's overall quality assessment risk for the population he or she sees. The overall quality of treatments being delivered by physicians and in hospitals 204 is continually monitored. In the hospital setting, the actual length of stay is measured against population averages for certain disease states. Statistically significant variance is immediately flagged for analysis and follow-up. In the physician's office setting, actual episode experience in targeted areas from therapies is measured against best practices. Additional best practice information per disease state is continually incorporated into the system 2 as it becomes available. The mass customization system 2 works with providers 202 to increase their risk-adjusted scores.

When a patient has been referred to a specialist, the primary care physician 204 is kept informed on an efficient basis of the progress of the patient, including treatments given, hospital admissions and discharges, and prescription drugs taken. This further empowers the primary care physician 204. When a substitute physician handles a physician's caseload, a special summary report is available so that quality treatment is continued. The primary care physician 204 is given a brief update of these healthcare encounters.

For example, in an existing healthcare model for measuring a physician's performance, health plans track outcomes in terms of the number of hospitalizations and emergency visits for his patients with chronic diseases. A physician takes care of a patient, and prescribes what he decides are necessary medications for the patient to achieve good outcomes. However, drug co-payments are such that some of the physician's patients cannot afford the co-payments, and these patients do not take the medications because they cannot afford the co-payment. One of the patients becomes sick, ends up the in the Emergency Room, and is admitted to the hospital where the patient incurs high levels of costs. The health plan classifies the physician as a "bad physician", and either penalizes him on his incentives or eliminates him from the preferred physician list. The result of the current system is that there is a disconnect between pharmacy plan design, physician care management, and overall patient clinical outcomes.

In contrast, the mass customization system 2 of a preferred embodiment of the present invention aligns incentives to optimize physician 204 performance and patient 202 clinical outcomes. The mass customization system 2 supports physicians to take good care of the patients and prescribe appropriately to achieve good quality outcomes. To measure a physician's performance, the health plan managers 18 track outcomes in terms the number of hospitalizations and emergency visits for patients with chronic diseases. The physician 204 cares for a patient 202 by prescribing what she decides are necessary medications for the patient 202 to achieve good outcomes. Based upon the mass customization data claims processing 14, co-payments are customized for the patient 202 so that the patient can afford the necessary medications. The patient 202 takes the necessary medication, and thereby does not need emergency room and hospital services. Thus, this mass customization system 2 averts the high costs for the health plan, while ensuring a better quality of life for the patient 202.

Health Plan Sponsor Value Maximization.

The aggregated approach to healthcare of the mass customization infrastructure 2 focuses on the participant 202 and the physician 204, with extreme focus given on outcomes. The sponsor web interface platform 24 assists the sponsors 200 in managing their healthcare expenditures much more efficiently. As discussed above with reference to FIG. 9, the system 2 has the ability to simulate healthcare utilization with or without certain plan benefits which enables the plan sponsor 200 to see the financial impact of plan decisions. On an ongoing basis, the system 2 of a preferred embodiment provides the sponsor 200 with action plans for monitoring and managing the health plan on an optimal basis. At predetermined time periods, e.g., annually, the system 2 administrators consult with the sponsor 200 to prepare a business plan for the upcoming plan year in order to empower the plan sponsor 200 with critical information for health plan decisions throughout the plan year.

Existing plans for certain healthcare areas require prior authorization or pre-certification for therapies to be provided. While the intent of these authorizations has been to ensure compliance with health plan coverages, in many instances, these required authorizations often have been smoke screens to deny or restrain therapy or treatment. The mass customization 2 of the present invention, which provides data models of many disease states, allows the probabilistic impact on a health plan to be determined. Therefore, many healthcare episodes that previously required prior authorization or pre-certification may be written into the health plan document itself. The document discloses to participants 202 in advance which items are excluded from plan coverage, and specifies the limited items that require prior authorization or pre-certification. The availability of this information in the plan documents lessens plan legal exposures, and thereby, healthcare costs. Mass customization 2 maintains the risk pooling concept of the prior art while diverging considerably from the insurance model of health benefits.

The mass customization system 2 offers several wellness benefit and lifestyle programs for sponsors 200 to incorporate into their health plans. Programs such as smoking cessation, weight reduction, senior citizen healthy lifestyles, etc., are specifically targeted to sub-sets 94, 96, 98, 100, 102 of the aggregate plan population, as shown in FIG. 5. Offering such programs has the opportunity to increase wellness of the patient populations 94, 96, 98, 100, 102. The system 2 healthcare data platform and analyzer 12 also analyzes data related to workers compensation, short term disability and long term disability with the same financial, statistical and clinical outcomes disciplines. As these areas have substantial impact on the plan sponsor 200, this analysis brings additional value to the sponsor 200.

Provider contracting has been a major failure of managed care. Contracting typically has been the responsibility of staff with limited process, financial, and statistical expertise. It is impossible for healthcare to be effectively delivered under such contracting arrangements. The mass customization system 2 of the preferred embodiment implements sophisticated data driven processes which analyze potential healthcare populations and which simulate utilization for different contractual provisions/exclusions. Use of the mass customization system 2 empowers contracting professionals to make decisive and precise decisions with respect to contractual terms, conditions and pricing.

Implementing Mass Customization.

Figure 8:
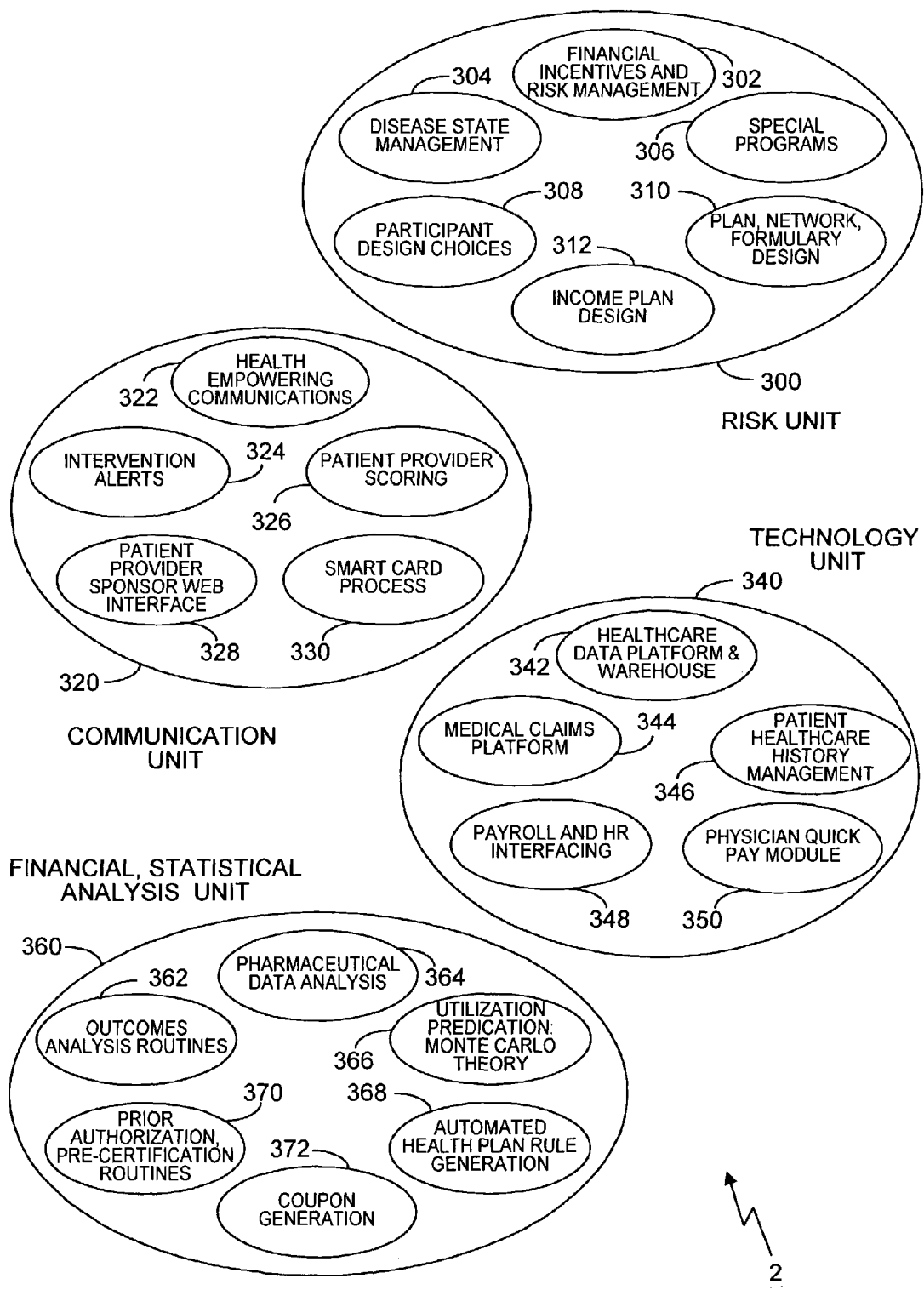
FIG. 8 is a diagram of the modules, platforms and processes incorporated into the mass customization infrastructure of a preferred embodiment.

The modules, platforms, and processes of the mass customization infrastructure 2, illustrated in FIGS. 1-7 and 9, may have a number of administrators and working units for managing the system 2. FIG. 8 illustrates an example administrative implementation of the mass customization infrastructure 2. In this example embodiment, the system 2 is administered utilizing a technology unit 340, a financial and statistical analysis unit 360, a communication unit 320, and a risk unit 300. Obviously, this example of the grouping of the modules, platforms and processes in the specified units 300, 320, 340, 360 is one of many such possible groupings and units combinations.

As illustrated in FIG. 8, and with reference to FIG. 1, the technology unit 340 is responsible for integrating massive amounts of data from disparate sources throughout healthcare for use in mining, analysis, simulations, forecasting and decision making. The technology unit 340 may include administration of the healthcare data platform and warehousing processes 342. The data platform 342 is in communication with data resources 40 for collecting data and storing the data in the data warehouse 16. The patient healthcare history management 346 is a process for continually collecting updated information on each participant/patient 202 in the system 2, and maintaining the information in a usable form for the other mass customization processes. For example, the payroll and human resources interfacing 348 process collects participant information from the employers' human resources and payroll software systems. The information content received by the system 2 most often is generic in nature or defined in very broad demographic terms. The technology unit 340, together with the statistical and communication units 360, 320, provides current, patient specific data, analysis and actionable information to assist in improving patient outcomes. The medical claims platform 344 and the physician quick pay module 350 gather the claim information for payment of medical and physician claims.

The communications unit 320 provides up-to-the-minute data and analysis for all healthcare stakeholders. The communication unit 320 is essential for communications between patients 202, providers 204, plan sponsors 200, and partners 206. The communication processes take maximum advantage of web portal technologies such as the patient provider sponsor web interface 328. The smart card process 330 also provides essential communications between the system 2, the patients 202, and the providers 204. In addition to patient clinical history, claims history and enrollment demographics, the system 2 communicates additional essential information to patients. Patients receive health empowering communications 322, either through a web interface or through the mail, that is specific to their healthcare, i.e, not generic information.

Intervention alerts 324, such as prescription drug information and direct to consumer programs, are provided to the patient 202. The availability of generic drug substitutes and preferred drugs in the formulary is communicated to patients when a branded drug is prescribed. Detailed information on a drug currently being taken as well as potential interactions with other drugs currently being prescribed is communicated. The intervention alerts process 324 also allows the patient 202 to note any side effects encountered with a particular drug. This has valuable information content for providers 204 as well as drug manufacturers 206. The intervention alert 324 may also be used to notify patients 202 that they are going to receive specialized monitoring and communication to assist them with their healthcare. These patients are those that meet certain predetermined criteria for inclusion in the specialized health improvement programs.

The patient provider scoring 326 provides feedback from the patient 202 after an important healthcare encounter. A patient 202 is given the opportunity to score the treatment offered and the manner in which the healthcare was delivered. This further empowers the patient 202 and enables the system 2 to provide valuable feedback to providers 204 to improve their operations. This scoring history is maintained on the data warehouse database 16.

The financial and statistical analysis unit 360 focuses on high-level statistical analysis of all healthcare encounters and views results relative to results for each disease state whose distribution curve has been simulated and optimized with Monte Carlo analysis 366. There exists in excess of three dozen different types of statistical distribution curves, each possessing very different characteristics and forecasting methodologies. As new data becomes available, distribution curves are updated with the new information, the health plan's financial forecast is updated, and treatment methodologies for the disease states are assessed.

The financial and statistical analysis unit 360 is responsible for continual monitoring, assessing and interpreting the data as it is received, and translating the data into actionable information. The unit 360 assesses outcomes 362 and updates plan results, e.g. generates health plan rules 368 and provides prior authorization and pre-certification 370 as well as coupon generation 372. Pharmaceutical analytical processes 364 break down all drug data sets into component parts, such as decomposition analysis for prescription drugs, which enables determination of the contributors to aggregate drug spend for each prescription drug.

The risk management unit 300 addresses risk of caring for patient populations by establishing plan, network, and formulary designs 310 that are presented to the sponsors 200. Risk is controlled by presenting the participants with appropriate plan design 308 during the enrollment process. The income plan design 312 of the preferred embodiment, which bases a participant's co-payment upon the participant's ability to pay, lowers plan risk by providing affordable healthcare to the participant.

The risk management unit 300 also manages risk sharing entities, such as captive insurance companies. Financial incentives and risk management processes 302 work to reduce reinsurance premiums, and lower sponsor errors and omissions insurance premiums. With comprehensive up-to-the minute financial and statistical analysis of claims data, the risk management unit 300 further impacts providers by consulting with them on their risk management operations. The analytical approach of the mass customization system 2, allows management of captive insurance subsidiaries with clients. The system optimizes sponsor reinsurance attachment points, e.g., deductibles, for their specific and aggregate healthcare reinsurance. Reinsurers are highly motivated by proactive steps to reign in potential high dollar claim exposures. By managing and monitoring special programs 306, e.g., for catastrophic care management and high frequency encounter disease states 304, the risk unit 300 brings the goals of the plan sponsors 200 in alignment with the reinsurance companies.

Although a preferred embodiment of the invention has been described above by way of example only, it will be understood by those skilled in the field that modifications may be made to the disclosed embodiment without departing from the scope of the invention, which is defined by the appended claims.

We claim:

1. An automated computerized method of customizing an individual participant's co-payment for a prescription medication, the method comprising:

providing a healthcare data platform, the platform comprising detailed individual healthcare information for a participant requesting a medication,
- wherein the information comprises data from third-party partners, providers and payers,
- and wherein the information comprises clinical information and financial information, and wherein the clinical information comprises at least one of: a detailed health history, prior healthcare utilization, one or more current health treatment, one or more current health concerns, genomic information, drug history, one or more laboratory values, and healthcare demographic data, and wherein the financial information comprises income data and financial demographic data,
- and wherein the information pertains to an individual participant;

receiving information regarding a prescription for a medication prescribed to the participant;

accessing the data platform to obtain medical history information of the participant including information regarding the one or more current health concerns of the participant and clinical implications of the prescription;

based on at least the medical history information and the clinical implications of the prescription, determining a current clinical value of the medication to the individual participant for addressing the one or more current health concerns of the participant, wherein a medical and drug history of the individual participant that does not support use of the medication results in a lower clinical value, and wherein a medical and drug history that does support use of the medication results in a high clinical value, and wherein a lower clinical value determines a higher copayment and a high clinical value determines a lower copayment;

accessing the data platform to obtain financial information associated with the participant including an income level associated with the participant, wherein a higher income level determines a higher copayment and a lower income level determines a lower copayment;

determining a copayment amount for the participant requesting a medication based on both the determined current clinical value of the medication to the participant and the income level associated with the individual; and wherein all steps of the method are performed by a mass customization infrastructure comprising a healthcare data platform and one or more computing devices, and wherein the infrastructure automatically integrates, analyzes and mines participant-specific clinical and financial data to determine the copayment for the participant requesting a medication in order to enhance the quality of healthcare.

* * * * *